United States Patent [19]

Peyman et al.

[11] Patent Number: 5,707,979
[45] Date of Patent: Jan. 13, 1998

[54] PHOSPHINIC ACID DERIVATIVES, THEIR PREPARATION AND THEIR USE

[75] Inventors: Anuschirwan Peyman, Kelkheim; Wilhelm Stahl, Frankfurt am Main; Karl-Heinz Budt, Kelkheim; Dieter Ruppert, Bad Soden; Henning Schüssler; Konrad Wagner, both of Frankfurt am Main, all of Germany

[73] Assignee: Hoechst Aktiengesellschaft, Frankfurt am Main, Germany

[21] Appl. No.: 495,977

[22] Filed: Jun. 28, 1995

[30] Foreign Application Priority Data

Jun. 30, 1994 [DE] Germany .................. 44 22 911.9

[51] Int. Cl.⁶ .................. A61K 31/675; C07F 9/6584
[52] U.S. Cl. .................. 514/110; 558/81; 562/9; 562/15; 564/12
[58] Field of Search .................. 514/110; 558/81; 562/15

[56] References Cited

FOREIGN PATENT DOCUMENTS

| | | |
|---|---|---|
| 0337714A2 | 10/1989 | European Pat. Off. |
| WO92/00954 | 1/1992 | WIPO |
| WO93/07128 | 4/1993 | WIPO |
| WO95/02582 | 1/1995 | WIPO |

OTHER PUBLICATIONS

J.A. Martin, "Recent Advances in the Design of HIV Proteinase Inhibitors," Antiviral Research, 17, pp. 265–278 (1992).

S.S. Abdel–Mequid, "Inhibitors of Aspartyl Proteinases," Medicinal Research Reviews, vol. 3, No. 6, pp. 731–778 (1993).

M. Lang et al., "HIV–1 Protease Inhibitors: Development, Status, and Potential Role in the Treatment of AIDS," Arch Phar., vol. 326, pp. 921–924 (1993).

P.Y.S. Lam et al., "Rational Design of Potent, Bioavailable, Nonpeptide Cyclic Ureas as HIV Protease Inhibitors," Science, vol. 263, pp. 380–384 (1994).

D.N. Srivastva et al., "Bioreversible Phosphate Protective Groups: Synthesis and Stability of Model Acyloxymethyl Phosphates," Bioorganic Chemistry, vol. 12, pp. 118–129 (1984).

Christian Périgaud et al., "Rational Design for Cytosolic Delivery of Nucleoside Monophosphates: Sate and DTE as Enzyme–Labile Transient Phosphate Protecting Groups," Bioorganic & Medicinal Chemistry Letters, vol. 3, No. 12, pp. 2521–2526 (1993).

A. Peyman et al., "$C_2$–symmetrische Inhibitoren der HIV–Protease auf Phosphinsäurebasis," Angew. Chem, vol. 105, No. 12, pp. 1852–1854 (1993).

B. Stowasser et al., "New Hybrid Transition State Analog Inhibitors of HIV Protease with Peripheric $C_2$–Symmetry," Tetrahedron Letters, vol. 33, No. 44, pp. 6625–6628 (1992).

L. Maier, "Organic Phosphorus Compounds. LXXI, Preparation, Properties, and Structure of Bis(Aminomethyl)phosphinic Acid, $(H_2NCH_2) P(O)OH$," J. of Organometallic Chem., vol. 178, pp. 157–169 (1979).

A. Peyman et al., "Non–Peptide–Based Inhibitors of Human Immunodeficiency Virus–1 Protease", Bioorganic & Medicinal Chemistry Letters, vol. 4, No. 21, (1994), pp. 2601–2604.

*Primary Examiner*—Michael G. Ambrose
*Attorney, Agent, or Firm*—Finnegan, Henderson, Farabow, Garrett & Dunner, L.L.P.

[57] ABSTRACT

Compounds of the formula I,

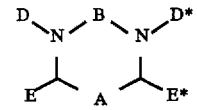

in which the symbols or substituents A, B, D, D*, E and E* have the meanings given in the specification, inhibit aspartyl proteases and are suitable for controlling viral diseases.

8 Claims, No Drawings

PHOSPHINIC ACID DERIVATIVES, THEIR PREPARATION AND THEIR USE

DESCRIPTION

The present invention relates to phosphinic acid derivatives, to their preparation and to their use. The novel compounds are used, for example, as inhibitors of aspartyl proteases, in particular as inhibitors of retroviral proteases, in particular of HIV protease. Pharmaceutical compositions containing these compounds are used for treating those diseases in which an improvement can be achieved by inhibiting aspartyl proteases, in particular for treating viral infections, very particularly infections with retroviruses which respond to such a treatment, in particular in infections due to human immunodeficiency virus (HIV).

The etiological cause of acquired immunodeficiency syndrome (AIDS) is the so-called human immunodeficiency virus (HIV). The AIDS epidemic has by now extended to virtually all countries. Current methods for treating AIDS involve compounds such as 3'-azido-3'-deoxythymidine (AZT), 2',3'-dideoxyinosine (ddI), 2',3'-dideoxycytidine (ddC) and other, in particular non-nucleosidic, inhibitors of reverse transcriptase (RT) which inhibit viral DNA synthesis. While AZT, which is the drug which has been tested therapeutically for the longest period of time, extends life expectancy when AIDS has fully developed from approximately 6 to, on average 24 months, it exhibits serious, toxic side effects which in many cases necessitate discontinuation of the therapy. A further problem is that HIV strains which are resistant both to AZT and also to ddI and ddC and non-nucleosidic RT inhibitors develop rapidly. For this reason, there is a pressing need for further approaches to HIV therapy. One of the most obvious targets for HIV chemotherapy is the so-called HIV protease, which is anaspartyl protease which cleaves vital polyproteins specifically and which is essential to the viral life cycle. Inhibition of the protease also inhibits replication of the virus.

A review of the state of the art in the field of HIV protease inhibitors is provided, for example, by: J. A. Martin, Antiviral Research 17 (1992) 265; S. S. Abdel-Meguid, Med. Res. Rev. 13 (1993) 731; M. Lang, J. Roesel, Arch. Pharm. 326 (1993) 921. The known inhibitors of HIV protease can be divided into two structural classes: peptide-based and non-peptide-based inhibitors.

The development of resistance in HIV strains, which is also seen when different HIV protease inhibitors are employed, and the frequently inadequate bioavailability and pharmacokinetics which are observed, particularly in the case of the peptide-based inhibitors, emphasize the need for new, preferably non-peptide-based, structures (for example WO 93/07128 or P. Y. S. Lam et al., Science 263 (1994) 380), which are able to inhibit HIV protease effectively.

Surprisingly, it has now been found that certain phosphinic acid derivatives are outstanding inhibitors of aspartyl proteases.

The invention therefore relates to compounds of the formula I

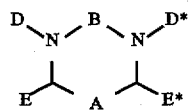

(I)

in which A is a radical of the formula IIa, IIb, IIc or IId

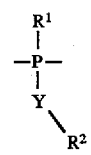  IIa

  IIb

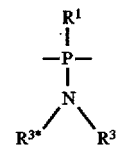  IIc

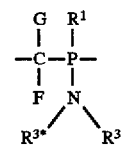  IId

Y is oxygen or sulfur;
$R^1$ is oxygen or sulfur;
$R^2$ is
  hydrogen;
  $(C_1-C_{20})$-alkyl,
  $(C_2-C_{20})$-alkenyl or alkynyl,
  $(C_7-C_{20})$-arylalkyl,
  $(C_6-C_{20})$-aryl,
  $(C_3-C_8)$-cycloalkyl,
all of which can optionally be substituted by up to 3 identical or different radicals from the group hydroxyl, alkyl, alkoxy, carboxyl, alkanoyloxy, alkoxycarbonyl, F, Cl, Br, I, amino, alkylamino or dialkylamino;
  an equivalent of a physiologically tolerated salt, or
  a residue of a phosphinic acid prodrug;
$R^3$ and $R^{3*}$ are, independently of each other,
  hydrogen,
  amino,
  $(C_1-C_{20})$-alkyl,
  $(C_2-C_{20})$-alkenyl or alkynyl,
  $(C_7-C_{20})$-arylalkyl,
  $(C_6-C_{20})$-aryl,
  $(C_3-C_8)$-cycloalkyl,
all of which can optionally be substituted by up to 3 identical or different radicals from the group hydroxyl, alkoxy, carboxyl, alkanoyloxy, alkoxycarbonyl, F, Cl, Br, I, amino, alkylamino or dialkylamino;
  or can together form a ring having from 3 to 6 carbon atoms, which ring can contain up to three hetero atoms such as, for example, oxygen or nitrogen;
G and F are, independently of each other,
  hydrogen,
  fluorine, chlorine or bromine,
  hydroxyl,
  O—$R^4$,
with the proviso that if G is hydroxyl, F should be hydrogen;
$R^4$ is
  hydrogen,
  $(C_1-C_{20})$-acyl,
  an hydroxy-prodrug group;

B is a radical of the formula IIIa or IIIb

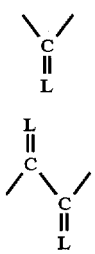

IIIa

IIIb where L is oxygen, sulfur or N—$R^5$;
where $R^5$ is
  hydroxyl,
  amino,
  $(C_1-C_4)$-alkyl,
  $(C_1-C_4)$-alkoxy,
  $(C_1-C_4)$-aminoalkyl,
  cyano,
  nitro,
  benzyloxy;
$R^5$ is preferably hydroxyl or amino;
D and D* are, independently of each other, hydrogen,
  $(C_1-C_{20})$-alkyl,
  $R^6$,
  $R^6-[(C_1-C_6)-alkyl]-$,
where alkyl can be saturated, unsaturated once or more than once, branched or unbranched, or cyclic, and where one or more carbon atoms can be replaced by hereto atoms such as, for example, oxygen, sulfur or nitrogen, and can optionally be substituted by up to 3 identical or different radicals $R^7$;
  where $R^6$ is isocyclic and/or heterocyclic ring systems comprising from 3 to 35 carbon atoms, saturated, unsaturated or partially saturated, which contain 3–9-membered rings which can be fused or be linked together by $(C_1-C_3)$-alkyl or heteroalkyl radicals, and where $R^6$ can be substituted once or twice by $R^7$;
  where the radicals $R^7$ are, independently of each other,
  $R^8$
  $-OR^8$,
  $-NR^9R^{10}$,
  oxo,
  $-C(O)OR^8$,
  $-C(O)NR^9R^{10}$,
  $-CN$, $-F$, $-Cl$, $-Br$, $-NO_2$,
  $-CH_2NR^9R^{10}$,
  $(C_2-C_6)$-alkoxyalkyl,
  $-S(O)_mR^8$,
  $-(C_1-C_6)$-alkyl-$S(O)_mR^8$,
  $-NHC(=NH)NHR^8$,
  $-C(=NH)NHR^8$,
  $-NR^9C(=O)R^8$,
  $=NOR^8$,
  $NR^9C(=O)OR^{10}$,
  $-OC(=O)NR^9R^{10}$,
  $-NR^9C(=O)NR^9R^{10}$;
  where m=0, 1 or 2, preferably 1 or 2;
  where $R^8$ is
    hydrogen,
    $(C_1-C_{18})$-alkyl,
    $(C_1-C_{18})$-alkenyl,
    $(C_1-C_{18})$-alkynyl,
    $(C_6-C_{12})$-aryl,
    $(C_6-C_{12})$-aryl-$(C_1-C_6)$-alkyl,
  where alkyl can be substituted once or twice by hydroxyl, $(C_1-C_4)$-alkoxy, F, Cl or Br;

$R^9$ and $R^{10}$ are, independently of each other, hydrogen, $(C_1-C_{18})$-alkyl, $(C_1-C_{18})$-alkenyl, $(C_1-C_{18})$-alkynyl, $(C_6-C_{12})$-aryl, $(C_6-C_{12})$-aryl-$(C_1-C_6)$-alkyl, where alkyl can be substituted once or more than once by hydroxyl, $(C_1-C_4)$-alkoxy, F, Cl or Br, $R^9$ and $R^{10}$ can, together with N, form a 4–7-membered ring; and E and E* are, independently of each other, hydrogen;
  $(C_1-C_7)$-alkyl, optionally substituted 1–3 times by F, Cl, Br or $(C_1-C_3)$-alkoxy, where alkyl can be saturated or unsaturated, branched or unbranched, and where one or two carbon atoms can be replaced by heteroatoms such as, for example, oxygen or nitrogen, and where alkyl can be substituted once or twice by $R^7$, where $R^7$ has the abovementioned meaning;
  $(C_6-C_{12})$-aryl-$(C_1-C_3)$-alkyl, optionally substituted 1–3 times by F, Cl, Br or $(C_1-C_3)$-alkoxy.

The compounds of the formula I are preferred in which
A is a radical of the formula IIa, IIb or IIc,
Y is oxygen,
$R^1$ is oxygen,
$R^2$ is
  hydrogen,
  $(C_1-C_6)$-alkyl,
  $(C_7-C_{13})$-arylalkyl,
  $(C_6-C_{12})$-aryl,
all of which can optionally be substituted by hydroxyl, $(C_1-C_{10})$-alkyl, $(C_1-C_3)$-alkoxy, F, Cl or Br;
  an equivalent of a physiologically tolerated salt,
  a residue of a phosphinic acid prodrug;
$R^3$ and $R^{3*}$ are, independently of each other,
  hydrogen,
  amino,
  $(C_1-C_4)$-alkyl,
  $(C_3-C_6)$-cycloalkyl,
both of which can optionally be substituted by hydroxyl, $(C_1-C_3)$-alkoxy, F, Cl or Br;
or can, together, form a ring having from 3 to 6 carbon atoms, which ring can also contain an oxygen or nitrogen atom, G and F are, independently of each other,
  hydrogen,
  fluorine,
  hydroxyl,
  $O-R^4$,
with the proviso that if G is hydroxyl, F should be hydrogen;
$R^4$ is hydrogen or $(C_1-C_4)$-acyl;
B is a radical of the formula IIIa, and L is oxygen;
D and D* are, independently of each other,
  hydrogen, or
  $R^6-[(C_1-C_6)-alkyl]-$,
where alkyl can be saturated or unsaturated, branched or unbranched, and where a carbon atom can be replaced by an oxygen or nitrogen atom and where alkyl can be substituted by $R^7$,
  where $R^6$ is
    $(C_6-C_{12})$-aryl, optionally substituted by $R^7$;
    $(C_3-C_{12})$-cycloalkyl, optionally substituted by $R^7$; a heterocyclic ring system comprising from 3 to 10 atoms, which system contains at least one nitrogen, oxygen or sulfur atom and is optionally substituted by $R^7$;
  where $R^7$ is
    $-R^8$,
    $-OR^8$, —$NR^9R^{10}$,
—CN, —F, —Cl, —Br,
—$CH_2NR^9R^{10}$, where $R^8$ is hydrogen, ($C_1$–$C_6$)-alkyl, optionally substituted by hydroxyl, ($C_1$–$C_4$)-alkoxy, F, Cl or Br;

($C_6$–$C_{12}$)-aryl, ($C_6$–$C_{12}$)-aryl-($C_1$–$C_6$)-alkyl;

$R^9$ and $R^{10}$ are, independently of each other, hydrogen, ($C_1$–$C_6$)-alkyl or phenyl;

E and E* are preferably hydrogen or benzyl, optionally substituted by F, Cl, Br or ($C_1$–$C_3$)-alkoxy.

The abovementioned compounds of the formula I are particularly preferred in which A is a radical of the formula IIa, IIb or IIc, $R^2$ is hydrogen, ($C_1$–$C_4$)-alkyl, an equivalent of a physiologically tolerated salt, or a residue of a phosphinic acid prodrug;

$R^3$ and $R^{3*}$ are hydrogen;

D and D* are, independently of each other, $R^6$—$CH_2$—, where $R^6$ is ($C_6$–$C_{12}$)-aryl which is unsubstituted or substituted once by $R^7$, where $R^7$ is, independently of each other,

—$R^8$,

—$OR^8$,

—F, —Cl or —Br, where $R^8$ is hydrogen, ($C_1$–$C_6$)-alkyl unsubstituted or substituted by hydroxyl or Br, and E and E* are hydrogen, or benzyl.

Furthermore, the abovementioned compounds of the formula I are of particular importance in which $R^2$ is hydrogen;

($C_1$–$C_4$)-alkyl, or an equivalent of a physiologically tolerated salt, and D is phenyl or benzyl which are substituted by $R^8$, where $R^8$ is hydrogen, ($C_1$–$C_3$)-alkyl, optionally substituted by hydroxyl or Br.

The following examples of substituents—unless otherwise defined—apply to substituents in single and combined or functionalized form (e.g. alkyl, aryl, alkoxy, alkylamino, etc.).

Examples of alkyl are methyl, ethyl, propyl, butyl, pentyl, hexyl, heptyl, octyl, iso-propyl, iso-butyl, decyl, dodecyl, tert-butyl, iso-pentyl, allyl, butenyl, pentenyl and hexenyl.

Examples of aryl are phenyl, 1-naphthyl and 2-naphthyl.

Examples of arylalkyl are benzyl, 2-naphthylmethyl, 1-naphthylmethyl, phenylethyl, phenylpropyl, 2-naphthylethyl, 2-naphthylpropyl, 1-naphthylethyl and 1-naphthylpropyl.

Examples of cycloalkyl are cyclopropyl, cyclobutyl, cyclopentyl, cyclohexyl and cycloheptyl.

Physiologically tolerated salts of compounds of the formula I are understood to mean both inorganic and organic salts, for example as described in Remington's Pharmaceutical Sciences (17th edition, page 1418 (1985)). Due to their physical and chemical stability, and their solubility, sodium salts, potassium salts, calcium salts and ammonium salts, inter alia, are preferred for acidic groups.

Phosphinic acid prodrug is understood to mean those groups which are converted under physiological conditions into the corresponding phosphinic acids ("bioreversible protective groups"). These are the same groups which are known to the person skilled in the art as phosphate prodrugs, e.g. acyloxyalkyl esters (D. Srivasta, D. Farquhar, Bioorg. Chem. 12 (1984) 118) such as, for example, pivaloyloxymethyl, pivaloyloxyethyl, pivaloyloxyisobutyl, acetyloxymethyl or acetyloxyethyl esters, or S-acylthioethanol esters (C. Perigaud et al., Bioorg. Med. Chem. Lett. 3 (1993) 2521) such as, for example, S-acetylthioethanol esters. Hydroxyl prodrugs are understood to mean those groups which are converted under physiological conditions into the corresponding hydroxyl group ("bioreversible protective groups"). Such groups are known to the person skilled in the art and are described, for example, in H. Bundgaard, Design of Prodrugs, Elsevier Science Publishers B. V., Amsterdam 1985.

The invention furthermore relates to a process for preparing compounds of the formula I which comprises (step 1) a compound of the formula IV

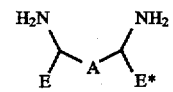

in which A, E and E* have the abovementioned meanings, being reacted with activated carbonic acid derivatives or oxalic acid derivatives to form cyclic ureas or cyclic oxalic acid diamides of the formula V

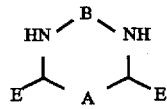

in which A, E, E* and B have the abovementioned meaning, and the resulting compounds subsequently (step 2) being alkylated to form compounds of the formula I, or which comprises the compounds of the formula IV being alkylated and the resulting compounds subsequently being cyclized with activated carbonic acid derivatives or oxalic acid derivatives to form compounds of the formula I.

The reaction is effected in accordance with methods known to the person skilled in the art (e.g. J. March, "Advanced Organic Chemistry", 3rd Ed., Wiley-Interscience, New York 1985).

Synthesis of the compounds of the formula IV has been described (e.g.: A. Peyman et al., Angew. Chem. 105 (1993) 1852; B. Stowasset et al., Tetrahedron Lett. 33 (1992) 6625). In step 1, reagents of the formula X—(C=L)—X' are employed for synthesizing the cyclic ureas, where X and X' are leaving groups and L is defined as above; the reaction is carried out under increased dilution in order to make the ring closure possible. Examples of X(C=L)X' are carbonyldiimidazole, thiocarbonyldiimidazole, phosgene, thiophosgene, diphenyl carbonate, diphenyl thiocarbonate and bistrichloromethyl carbonate. Activated derivatives of oxalic acid, preferably oxalyl chloride, are employed under the above-mentioned conditions for synthesizing cyclic oxalic acid diamides.

Where appropriate, functional groups (not, however, the terminal amino groups) in the diamines IV are protected by methods known to the person skilled in the art (e.g. Greene, Wuts, "Protective Groups in Organic Synthesis", J. Wiley, New York 1991); for example, hydroxyl groups are protected with acyl groups, such as acetyl, or phosphinic acids are protected, where appropriate, as esters, such as methyl esters.

In step 2, the compounds of the formula V are converted by alkylation into compounds of the formula I. The alkylation is also effected, for example, in accordance with methods known to the person skilled in the art, by reaction with a base and an alkylating reagent, where appropriate using phase transfer catalysis (E. V. Dehmlow, S. S. Dehmlow, "Phase Transfer Catalysis", 3rd Ed., VCH, Weinheim 1993) in a suitable organic solvent. D-Y or D*-Y compounds, in which Y is a leaving group such as halogen, triflate or mesylate, are preferred alkylating reagents. Preferred solvents are polar, aprotic solvents such as DMSO. Where appropriate, functional groups in D-Y or D*-Y are protected using methods known to the person skilled in the art (e.g. Greene, Wuts, "Protective Groups in Organic Synthesis", J. Wiley, New York 1991). Examples of protective groups which are preferred for the hydroxyl groups are trimethylsilylethoxymethyl (SEM), methoxyethoxymethyl (MEM), methoxymethyl (MOM) and 4-methoxyphenyl (MOP).

At the end of the synthesis, known methods are likewise used to eliminate the protective groups once again.

The phosphinamides are synthesized from the phosphinic acids in accordance with known methods, for example by conversion into the phosphinyl chlorides and subsequent aminolysis, where appropriate prior to eliminating the protective groups.

The invention also relates to the use of the compounds of the formula I as medicines, and to pharmaceutical preparations which contain these compounds.

Pharmaceutical preparations contain an effective quantity of the active compound of the formula I together with an inorganic or organic pharmaceutically utilizable excipient.

The pharmaceutical preparations are prepared in dissolution, mixing, granulation or coating methods which are known per se.

For an oral use form, the active compounds are mixed with the additives which are customary for this purpose such as excipients, stabilizers or inert diluents, and brought into suitable forms for administration, such as tablets, coated tablets, hard gelatin capsules, aqueous, alcoholic or oily suspensions, or aqueous, alcoholic or oily solutions, using customary methods. Gum arabic, magnesium hydroxide, magnesium carbonate, potassium phosphate, lactose, glucose, magnesium stearyl fumarate or starch, in particular corn starch, can be used as inert excipients. In this context, the preparation can be carried out as a dry granulate or a wet granulate. Examples of suitable oily excipients or solutions are vegetable or animal oils, such as sunflower oil and cod-liver oil. For subcutaneous or intravenous administration, the active compounds, or their physiologically tolerated salts, are brought into solution, suspension or emulsion, if desired using the substances which are customary for this purpose, such as solubilizers, emulsifiers or further auxiliary substances. Examples of suitable solvents are: water, physiological saline solution or alcohols, for example ethanol, propanediol or glycerol, and also sugar solutions, such as glucose or mannitol solutions, or else a mixture comprising the different solvents mentioned. It is likewise possible to employ injectable delayed-release preparations. Examples of drug forms which can be used are oily crystal suspensions, microcapsules, rods or implants, with the latter being composed of tissue-tolerated polymers, in particular biodegradable polymers, such as, for example, those based on polylactic acid/polyglycolic acid copolymers or human albumin.

The present invention furthermore relates to a process for treating those diseases in which an improvement can be achieved by inhibiting aspartyl proteases, in particular viral infections, very particularly infections with retroviruses which respond to such a treatment. The process includes administering a compound of the formula I to an infected patient. The process relates, in particular, to infections caused by HIV type 1. Administration of an effective dose can be carried out orally, parenterally, transdermally, intravenously, intramuscularly, rectally or by inhalation. The dosage unit is between 0.05 and 100 mg/kg of body weight; it is typically from 50 to 1000 mg and is administered once to ten times daily in the case of an acute or chronic infection. The necessary dosage is readily determined by the person skilled in the art and depends on age, weight and condition of the patient and on the mode of administration. The combination therapy which is described in Eur. Pat. Appl. No. 337 714, pp. 42–47, can also be used.

The present invention is explained in more detail by the subsequent exemplary embodiments and by the content of the patent claims.

EXAMPLES 1) 2,6-Dibenzyl-1-hydroxy-3,5-diaza-4-oxophosphorinone-1-oxide (racemate composed of [2S,6S] and [2R,6R])

104.5 mg (0.64 mmol) of N,N'-carbonyldiimidazole (CDI) in 3 ml of absol. Dichloromethane (DCM) were slowly added dropwise to a solution of 100 mg (0.293 mmol) of bis(1-amino-2-phenylethyl)phosphinic acid hydrochloride (racemate) and 94.8 mg (0.733 mmol) of ethyldiisopropylamine in 100 ml of absol. DCM. The mixture was stirred at room temperature (RT) for 48 hours, and a further 104.5 mg (0.64 mmol) of CDI were then added. After a further 24 hours, the solvent was evaporated off in vacuo and the residue was partitioned between DCM and water; the aqueous phase was adjusted to pH 3 with 1N HCl and the phases were washed reciprocally with DCM and water; the organic phase was dried, filtered and concentrated. The residue was stirred up between ethyl acetate (EA) and water, and filtered off with suction.

Yield: 12 mg,

MS (ES$^+$): 331 (M+H$^+$, 30%)

2) 2,6-Dibenzyl-1-methoxy-3,5-diaza-4-oxophosphorinone-1-oxide (racemate composed of [2S,6S] and [2R,6R])

129.7 mg (0.8 mmol) of CDI in 4 ml of absol. DCM were slowly added dropwise to 169.8 mg (0.533 mmol) of methyl bis(1-amino-2-phenylethyl)phosphinate (racemate) in 350 ml of absol. DCM. The mixture was stirred at RT for 24 hours, and a further 86.4 mg of CDI in 2 ml of DCM were then added and the mixture was stirred at RT for a further 48 hours. Working-up subsequently took place as described in Example 1 (pH from 5 to 6), and the residue was purified by chromatography on silica gel, DCM/methanol 96:4.

Yield: 61.2 mg;

MS (EI): 345 (M+H$^+$, 100);

$^1$H-NMR (200 MHz, DMSO): 2.70–3.09 (m, 4H, CH$_2$—Ar); 3.46 & 3.51 (in each case s, 3H, OCH$_3$); 3.48–3.62 (m, 1H, P—CH); 3.66–3.82 (m, 1H, P—CH); 5.96 (dt, 1H, NH); 6.40 (dt, 1H, NH); 7.18–7.37 (m, 10H, Ar—H).

3) 1-Hydroxy-3,5-diaza-4-oxophosphorinone-1-oxide triethylammonium salt

Firstly, 303 mg (3 mmol) of triethylamine, and then 622 ml of phosgene (20% in toluene), were added dropwise, at 0° C., to a solution of 340 mg (1 mmol) of bis(N-trimethylsilylaminomethyl)-O-trimethylsilylphosphinate (L. Maier, J. Organomet. Chem. 178 (1979) 157) in 50 ml of absol. toluene; the mixture was then stirred at 0° C. for 3 hours and at RT for 20 hours. 10 ml of water was then added to it and the whole was concentrated to dryness in vacuo. The residue was stirred up with methanol, filtered and chromatographed on silica gel (DCM/methanol 9:1 and then 1:1). The product was triturated with ether and filtered off with suction.

Yield: 35.2 g

MS (ES$^+$): m/e=151 (M+H$^+$, 10%), 102 (100%)

$^1$H-NMR (200 MHz, DMSO): 5.98 (d, 2H, NH); 2.90 (dd, $J_1$=25 Hz, $J_2$=4 Hz, 4H, P—CH$_2$)

4) 1-Benzyloxy-3,5-dibenzyl-3,5-diaza-4-oxophosphorinone-1-oxide 30 mg (0.2 mmol) of 1-hydroxy-3,5-diaza-4-oxophosphorinone-1-oxide (Example 3) were dissolved, together with 78.2 mg (0.24 mmol) of cesium carbonate, in 2 ml of water and 4 ml of methanol, and this solution was boiled under reflux for 6 hours. It was then evaporated to dryness on a rotary evaporator. The residue was suspended in 4 ml of absol. DMF, and 61.6 mg (0.36 mmol) of benzyl bromide were then added to this suspension, with the whole being stirred at RT for 72 hours and then at 50° C. for 4 hours. The solvent was distilled off in vacuo, and the residue was partitioned between EA and an aqueous solution of NaCl, and the phases were then separated. The organic phase was dried, filtered and concentrated, and the residue was chromatographed on silica gel (toluene/EA 3:7).

Yield: 7 mg

MS (EI): m/e=421 (M+H$^+$, 100%)

$^1$H-NMR (200 MHz, DMSO): 3.48–3.63 (m, 4H, P—CH$_2$); 4.45 (d, J=4.45 Hz, 4H, N—CH$_2$); 4.95 (d, J=9 Hz, 2H, O—CH$_2$); 7.22–7.44 (m, 15H, Ar—H)

5) 1-(2-(2-Phenylethyl))benzyloxy-3,5-di(2-(2-phenylethyl)) benzyl-3,5-diaza-4-oxophosphorinone-1-oxide This compound is synthesized, as described in Example 4, from 30 mg of 1-hydroxy-3,5-diaza-4-oxophosphorinone-1-oxide and 2-(2-phenylethyl)benzyl bromide. Chromatography takes place on silica gel using toluene/EA 98:2.

Yield: 11.7 mg

MS (EI): m/e=733 (M+H$^+$, 15%)

6) [2R, 6S]-Dibenzyl-1-hydroxy-3,5-diaza-4-oxophosphorinone-1-oxide

This compound is synthesized, in analogy with Example 1, from (0.293 mmol) of meso-bis(1-amino-2-phenylethyl) phosphinic acid hydrochloride.

Yield: 46%;

MS (FAB): m/e=353 (M+Na$^+$), 331 (M+H$^+$);

$^1$H-NMR (200 MHz, DMSO): 2.64–2.90 (m, 2H, CH$_2$—Ar); 2.98–3.19 (m, 2H, CH$_2$—Ar); 3.44–3.63 (m, 2H, P—CH$_2$); 5.90 (d, 2H, NH); 7.13–7.40 (m, 10H, Ar—H).

7) [2R, 6S]-Dibenzyl-1-methoxy-3,5-diaza-4-oxophosphorinone-1-oxide

This compound is synthesized, in analogy with Example 2, from methyl meso-bis(1-amino-2-phenylethyl) phosphinate;

Yield: 49%

MS (FAB/LiCl): m/e=351 (M+Li$^+$, 80%);

$^1$H-NMR (200 MHz, DMSO): 2.74–3.10 (m, 4H, CH$_2$—Ar); 3.15 & 3.64 (in each case d, 3H, OCH$_3$); 3.59–3.97 (m, 2H, P—CH); 5.96 (dt, 1H, NH); 6.07 & 6.31 (in each case d, 2H, NH); 7.16–7.40 (m, 10H, Ar—H).

8) ([2R],3,5, [6S])-Tetrabenzyl-1-benzyloxy-3,5-diaza-4-oxophosphorinone-1-oxide 15.4 mg (0.32 mmol) of 50% NaH were suspended in 3 ml of absol. dimethyl sulfoxide (DMSO), and this suspension was firstly stirred at 65° C. for 1.5 hours and then cooled down to 10° C. 10.5 mg (0.032 mmol) of [2R, 6S]-dibenzyl-1-hydroxy-3,5-diaza-4-oxophosphorinone-1-oxide (Example 6) in 1.5 ml of absol. DMSO were added and this mixture was then stirred at 15° C. for 10 minutes; 109.5 mg (0.64 mmol) of benzyl bromide were then added. This mixture was stirred at RT for 17 hours, and 38.4 mg (0.64 mmol) of glacial acetic acid/toluene were then added all at once while cooling. The solvent was distilled off in vacuo and the residue was partitioned between EA and water. The phases were separated and washed reciprocally with EA and water and then with an aqueous solution of NaCl. The organic phase was dried, filtered and concentrated. The residue was chromatographed on silica gel. (Toluene/EA 7:3).

Yield: 7.2 mg;

MS (ES$^+$): m/e=601 (M+H$^+$, 100%);

9) ([2R],3,5,[6S])-Tetrabenzyl-1-methoxy-3,5-diaza-4-oxophosphorinone-1-oxide

This compound is synthesized, in analogy with Example 8, from [2 R, 6 S]-dibenzyl-1-methoxy-3,5-diaza-4-oxophosphorinone-1-oxide (Example 7). Chromatography is carried out on silica gel using toluene/EA, from 95:5 to 6:4.

Yield: 76%;

MS (FAB): m/e=525 (M+H$^+$, 100%);

$^1$H-NMR (200 MHz, DMSO): 2.92 (d, 3H, OCH$_3$); 2.98–3.15 (m, 2H, CH$_2$—Ar); 3.36–3.72 (m, 6H, P—CH & N—CH$_2$ & CH$_2$—Ar); 5.17 (dd, 2H, N—CH$_2$); 6.95–7.43 (m, 20H, Ar—H).

10) ([2R],3,5,[6S])-Tetrabenzyl-1-hydroxy-3,5-diaza-4-oxophosphorinone-1-oxide a) Hydrolysis with bromotrimethylsilane 32.4 mg of ([2R],3,5,[6S])-tetrabenzyl-1-methoxy-3,5-diaza-4-oxophosphorinone-1-oxide (Example 9) were dissolved in 3 ml of dioxane, and 1.5 ml of bromotrimethylsilane was added to this solution. The mixture was stirred at RT for 20 hours and the bromotrimethylsilane was then slowly distilled off in vacuo. Coevaporation with toluene was carried out three times. The residue was stirred for 1 hour in 1 ml of THF/1 ml of glacial acetic acid/1 ml of water, and this mixture was then evaporated, with fuming, with ethanol. The residue was chromatographed on silica gel (EA/methanol 8:2).

Yield: >95%

MS (FAB): m/e=533 (M+Na$^+$, 30%); 511 (M+H$^+$, 70%)

$^1$H-NMR (200 MHz, DMSO): 2.82–3.00 (m, 2H, CH$_2$—Ar); 3.08–3.40 (m, 2H, CH$_2$—Ar); 3.45–3.73 (m, 4H, P—CH & N—CH$_2$); 4.89 (d, 2H, N—CH$_2$); 7.03–7.36 (m, 20H, Ar—H).

b) Hydrolysis with HBr 1 mg of ([2R],3,5,[6S])-tetrabenzyl-1-methoxy-3,5-diaza-4-oxophosphorinone-1-oxide (Example 9) was dissolved in 1 ml of HBr/glacial acetic acid (33%), and this solution was stirred at 60° C. for 6 hours. The solvent was distilled off in vacuo, and the residue was then coevaporated three times with toluene.

MS (FAB): m/e=533 (M+NA$^+$, 30%); 511 (M+H$^+$, 70%)

11) ([2R], [6S])-Dibenzyl-3,5-(4-trimethylsilylethoxybenzyl)-1-methoxy-3,5-diaza-4-oxophosphorinone-1-oxide This compound is synthesized, in analogy with Example 9, from [2R,6S]-dibenzyl-1-methoxy-3,5-diaza-4-oxophosphorinone-1-oxide (Example 7) and 4-trimethylsilylethoxybenzyl bromide;

Yield: 64%;

MS (FAB/LiCl): m/e=851.5 (M+Li$^+$, 100%);

12) ([2R],[6S])-Dibenzyl-3,5-(4-hydroxymethylbenzyl)-1-hydroxy-3,5-diaza-4-oxophosphorinone-1-oxide 40 mg (0.0473 mmol) of ([2R],[6S])-dibenzyl-3,5-(4-trimethylsilylethoxymethylbenzyl)-1-methoxy-3,5-diaza-4-oxophosphorinone-1-oxide (Example 11) were dissolved in 3 ml of dioxane. 1.5 ml of bromotrimethylsilane were added to this solution, which was stirred at room temperature for 20 hours. The solvent was distilled off in vacuo, and the residue was stirred up together with 1 ml of tetrahydrofuran (THF), 1 ml of glacial acetic acid and 1 ml of water for 1 hour; this mixture was then concentrated and the residue coevaporated three times with toluene, with the subsequent residue being chromatographed on silica gel (EA/methanol from 8:2 to 6:4).

Yield: 60%;

MS (FAB): m/e=593 (M+Na$^+$, 50%); 571 (M+H$^+$, 20%)

13) ([2R],[6S])-Dibenzyl-3,5-(4-bromomethylbenzyl)-1-hydroxy-3,5-diaza-4-oxophosphorinone-1-oxide 4.5 mg of ([2R],[6S])-dibenzyl-3,5-(4-trimethylsilylethoxymethylbenzyl)-1-methoxy-3,5-diaza-4-oxo-phosphorinone-1-oxide (Example 11) were dissolved in 1 ml of 33% HBr/glacial acetic acid, and this solution was stirred at RT for 16 hours. After that, coevaporation took place three times with toluene. The residue was stirred up with ether and the ether was separated off after settling.

MS (FAB): 699, 697, 695 (M+H$^+$)

14) 2,6-Dibenzyl-3,5-(2-naphthylmethyl)-1-methoxy-3,5-diaza-4-oxophosphorinone-1-oxide (racemate composed of [2S, 6S] and [2R, 6R])

This compound is synthesized, in analogy with Example 8, from 2,6-dibenzyl-1-methoxy-3,5-diaza-4-oxophosphorinone-1-oxide (racemate composed of [2S, 6S] and [2R, 6R], Example 2) and 2-naphthylbromomethane.

MS (ES$^+$): m/e=625 (M+H$^+$, 100%);

$^1$H-NMR (200 MHz, DMSO): 2.78–3.10 (m, 4H, CH$_2$-naphth); 3.20 (d, 3H, OCH$_3$); 3.35 & 3.64 (in each case d, 2H, P—CH); 3.84–4.12 (m, 2H, N—CH$_2$); 4.64–4.81 (m, 2H, N—CH$_2$); 7.02–8.00 (m, 28H, Ar—H).

15) 7-(RS)-Acetoxy-2(S), 6(S)-dibenzyl-1,4-dioxo-1-methoxy-1-phospha-3,5-diazepine 15a) Methyl (1-(N-benzyloxycarbonylamino)-2(S)-phenethyl)-(1(RS)-acetoxy-2(S)-(N-benzyloxycarbonylamino) phenpropyl)-(RS)-phosphinate Methyl (1-amino-2(S)-phenethyl)-(2(R)-amino-1(RS)-hydroxy-2-phenpropyl)-(RS)-phosphinate(2.9 g, 4.6 mmol) (synthesized in analogy with B. Stowasser et al. Tetrahadron Lett. 44 (1992) 6625) is heated at from 50° to 60° C. for 5 hours in a mixture of pyridine and acetic anhydride (5 ml each), and then concentrated. The residue is taken up in ethyl acetate, and this solution is extracted with a saturated solution of ammonium chloride and with a saturated solution of sodium hydrogen carbonate. Purification is effected by means of chromatography on silica gel using a toluene/ethyl acetate gradient (3:11:1).

Yield: 2.9 g (4.4 mmol), 95%.

MS (ES$^+$): m/e=672 (M+H$^+$=673, 100%)

15b) Methyl (1-amino-2(S)-phenethyl)-(1(RS)-acetoxy-2(R)-amino-2-phenpropyl)-(RS)-phosphinate Methyl (1-(N-benzyloxycarbonylamino)-2(S)-phenethyl)-(1(RS)-acetoxy-2(S)-(N-benzyloxycarbonylamino) phenpropyl)-(RS)-phosphinate (2.9 g, 4.4 mmol) is dissolved in anhydrous ethanol (15 ml), and palladium on charcoal (5%, 100 mg) is added to this solution, which is stirred in a hydrogen atmosphere for 5 hours. The same amount of catalyst is added once again after 2 hours. Subsequently, the catalyst is filtered off and the solution is concentrated, with the residue being chromatographed on silica gel using an ethyl acetate/methanol gradient (4:14:2).

Yield: 1.6 g (3.9 mmol), 90%.

FAB-MS (MeOH, NBA, LiCl): m/e=404 (M+Li$^+$=411, 100%)

15c) 7-(RS)-Acetoxy-2(S), 6(S)-dibenzyl-1,4-dioxo-1-methoxy-1-phospha-3,5-diazepine Methyl (1-amino-2(S)-phenethyl)-(1(RS)-acetoxy-2(R)-amino-2-phenpropyl)-(RS)-phosphinate (1.6 g, 3.9 mmol) and carbonyldiimidazole (720 mg, 4.2 mmol) are stirred at room temperature for 45 hours in anhydrous dichloromethane (50 ml), and this mixture is then concentrated. For purification, the residue is chromatographed on silica gel using an ethyl acetate/methanol gradient (6:14:1).

Yield: 1.14 g (2.7 mmol), 70%.

MS (ES$^+$): m/e=430 (M+H$^+$=431, 100%)

16) 7-(RS)-Acetoxy-2(S), 3,5,6(S)-tetrabenzyl-1,4-dioxo-1-methoxy-1-phospha-3,5-diazepine Sodium hydride (500 mg) is added to dimethyl sulfoxide (50 ml), and this mixture is stirred at 65° C. for 1.5 hours. After 7-(RS)-acetoxy-2(S), 6(S)-dibenzyl-1,4-dioxo-1-methoxy-1-phospha-3,5-diazepine (1.14 g, 2.7 mmol) have been added, 10 minutes are allowed to pass and benzylbromide (3 ml) is then added dropwise. After one hour at 30° C., acetic acid is added to the mixture, which is then diluted with ethyl acetate and extracted with a saturated solution of sodium hydrogen carbonate. For purification, chromatography takes place on silica gel using an ethyl acetate/methanol gradient (25:14:1).

Yield: 1.0 g (1.6 mmol), 60%.

FAB-MS (MeOH, NBA, LiCl): m/e=610 (M+Li$^+$=617, 100%)

17) 7-(RS)-Acetoxy-2(S), 3,5,6(S)-tetrabenzyl-1,4-dioxo-1-hydroxy-1-phospha-3,5-diazepine 7-(RS)-Acetoxy-2(S), 3,5,6(S)-tetrabenzyl-1,4-dioxo-1-methoxy-1-phospha-3,5-diazepine (1.0 g, 1.6 mmol) is stirred for from 1 to 2 days in a mixture of dioxane (8 ml) and bromotrimethylsilane (4 ml). After the solution has been concentrated, purification takes place by the residue being chromatographed on silica gel using an ethyl acetate/methanol gradient (4:1) containing 4% acetic acid.

Yield: 530 mg (1.1 mmol), 65%

FAB-MS (MeOH, NBA, LiCl): m/e=582 (M+2Li$^+$ −H=595, 100%).

18) 2(S), 3,5,6(S)-Tetrabenzyl-1,4-dioxo-1,7-(RS)-dihydroxy-1-phospha-3,5-diazepine 7-(RS)-Acetoxy-2(S), 3,5,6(S)-tetrabenzyl-1,4-dioxo-1-hydroxy-1-phospha-3,5-diazepine (530 mg, 1.1 mmol) are dissolved in anhydrous dichloromethane (3 ml), and this solution is then cooled down to 78° C., after which a solution of diisobutylaluminumhydride in dichloromethane (2.5 equivalents) is added. After 2 hours, methanol (1 ml) is added, and the mixture is then diluted with ethyl acetate and extracted with a saturated solution of potassium sodium tartrate; for purification, chromatography takes place on silica gel using an ethyl acetate/methanol gradient (5:12:1) containing 4% acetic acid.

Yield: 430 mg (0.8 mmol), 72%.

FAB-MS (MeOH, NBA, LiCl): m/e=540 (M+2Li$^+$–H= 553, 100%).

19) 2,6-Dibenzyl-3,5-(2-naphthylmethyl)-1-hydroxy-3,5-diaza-4-oxophosphorinane-1-oxide (racemate composed of [2S,6S] and [2R,6R])

This compound is synthesized, in analogy with Example 10a, from 2,6-dibenzyl-3,5-(2-naphthylmethyl)-1-methoxy-3,5-diaza-4-oxophosphorinane-1-oxide (racemate composed of [2S, 6S] and [2R, 6R], Example 14);

Yield: 90%

MS (ES$^+$): m/e=633 (M+Na$^+$, 10%), 611 (M+H$^+$, 30%);

$^1$H-NMR (200 MHz, CDCl$_3$): 2.63–3.68 (m, 6H, Ar—CH$_2$ & P—CH); 3.40–3.69 (m, 2H, N—CH$_2$); 4.60–4.85 (m, 2H, N—CH$_2$); 6.62 –7.88 (m, 28 H, Ar—H).

20) 2,5-Dibenzyl-1-hydroxy-3,5-diaza-4-oxophosphorinane-1-oxide (racemate composed of [2S,6S] and [2R,6R]).

This compound is synthesized, in analogy with Example 10a, from 2,6-dibenzyl-1-methoxy-3,5-diaza-4-oxophosphorinane-1-oxide (racemate composed of [2S, 6S] and [2R,6R], Example 2) by reaction with bromotrimethylsilane.

MS (ES$^+$): m/e=331 (M+H$^+$, 30%);

$^1$H-NMR (200 MHz, DMSO): 2.48–2.75 (m, 2H, P—CH); 2.97–3.21 (m, 4H, Ar—CH$_2$); 4.87 (d, 2H, NH); 7.10–7.39 (m, 10H, Ar—H).

21) ( [2R], [6S])-Dibenzyl-3,5-(4-[4-methoxyphenoxy]-methylbenzyl)-1-methoxy-3,5-diaza-4-oxophosphorinane-1-oxide (racemate composed of [2S, 6S] and [2R, 6R])

This compound is synthesized, in analogy with Example 8, from 2,6-dibenzyl-1-methoxy-3,5-diaza-4-oxophosphorinane-1-oxide (racemate composed of [2S, 6S] and [2R, 6R], Example 2) and 4-[4-methoxyphenoxy] methylphenylbromomethane.

Yield: 67%

MS (FAB): 797.3 (M+H$^+$);

$^1$H-NMR (200 MHz, CDCl$_3$): 2.82–3.10 (m, 4H, CH$_2$—Ar); 3.15 (d, 3H, OCH$_3$); 3.30–3.55 (m, 2H, P—CH); 3.75 (s, 6H, OCH$_3$); 3.75–4.00 (m, 2H, N—CH$_2$); 4.78–4.99 (m, 2H, N—CH$_2$); 5.00 (d, 4H, CH$_2$—O); 6.72–7.43 (m, 26H, Ar—H).

22) ( [2R], [6S])-Dibenzyl-3,5-(4-bromomethylbenzyl)-1-hydroxy-3,5-diaza-4-oxophosphorinane-1-oxide (racemate composed of [2S,6S] and [2R,6R])

This compound is synthesized, in analogy with Example 10b, from ([2R], [6S])-dibenzyl-3,5-(4-(4-methoxyphenoxymethylbenzyl)-1-hydroxy-3,5-diaza-4-oxophosphorinane-1-oxide (racemate composed of [2S, 6S] and [2R, 6R]); however, in contrast to Example 10b, the solution was stirred at 0° C. for 74 h.

Yield: 88%

MS (FAB):m/e=MS (FAB): 699.1, 697.1, 695.1 (M+H$^+$)

23) ([2R],[6S])-Dibenzyl-3,5-(4-hydroxymethylbenzyl)-1-hydroxy-3,5-diaza-4-oxophosphorinane-1-oxide (racemate composed of [2S,6S] and [2R,6R])

6 mg of ([2R],[6S])-dibenzyl-3,5-(4-bromomethylbenzyl)-1-hydroxy-3,5-diaza-4-oxophosphorinane-1-oxide (Example 22) were dissolved in 1 ml of dioxane/water, and 13 mg of CaCO$_3$ were added to this solution. The mixture was then stirred at 110° C. for 3 h. The solvent was evaporated off and 10 ml of ethyl acetate were added to the residue; 0.39 ml of 1N HCl were added to this mixture, which was stirred for 10 min. The phases were separated and washed reciprocally with ethyl acetate and a solution of NaCl. The organic phase was dried, filtered and concentrated. The residue was triturated with n-pentane and filtered off with suction.

Yield: 4 mg; MS (FAB): 593.2 (M+Na$^+$); 571.2 (M+H$^+$).

24) Test for inhibition of the HIV protease

The test for inhibition of the HIV protease was carried out as described in EP 0 428 849 A2. The following IC$_{50}$ values indicate the concentration at which the activity of the enzyme is halved;

Example 19: IC$_{50}$=320 nM

Example 12: IC$_{50}$=4800 nM

Example 13: IC$_{50}$=18000 nM

Example 10: IC$_{50}$=50000 nM

Example 23: IC$_{50}$=240 nM

Examples Table

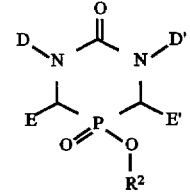

| Ex. No. | Stereo-chemistry | R$^2$ | E,E* | D,D* |
|---|---|---|---|---|
| 1 | rac.R,R/S,S | H | Benzyl | H |
| 2 | rac.R,R/S,S | CH$_3$ | Benzyl | H |
| 3 | — | NHEt$_3$ | H | H |
| 4 | — | Benzyl | H | H |
| 5 | — | (2-Pentyl-ethyl) benzyl | H | 2-(2-Phenylethyl)-benzyl |
| 6 | R,S | H | Benzyl | H |
| 7 | R,S | CH$_3$ | Benzyl | H |
| 8 | R,S | Benzyl | Benzyl | Benzyl |
| 9 | R,S | CH$_3$ | Benzyl | Benzyl |
| 10 | R,S | H | Benzyl | Benzyl |
| 11 | R,S | CH$_3$ | Benzyl | 4-Trimethylsilyl-ethoxymethylbenzyl |
| 12 | R,S | H | Benzyl | 4-Hydroxymethyl-benzyl |
| 13 | R,S | H | Benzyl | 4-Bromomethyl-benzyl |
| 14 | rac.R,R/S,S | CH$_3$ | Benzyl | 2-Naphthyl |
| 19 | rac.R,R/S,S | H | Benzyl | 2-Naphthyl |
| 20 | rac.R,R/S,S | H | Benzyl | H |
| 21 | rac.R,R/S,S | CH$_3$ | Benzyl | 4-(4-Methoxy-phenoxy)benzyl |
| 22 | rac.R,R/S,S | H | Benzyl | 4-Bromomethyl-benzyl |
| 23 | rac.R,R/S,S | H | Benzyl | 4-Hydroxymethyl-benzyl |

-continued

Examples Table part II

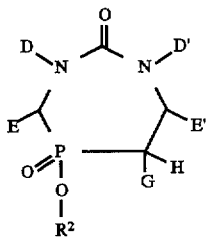

| No. | G | Stereo-chemistry | $R^2$ | E,E* | D,D* |
|---|---|---|---|---|---|
| 15 | OAcetyl | S,S | $CH_3$ | Benzyl | H |
| 16 | OAcetyl | S,S | $CH_3$ | Benzyl | Benzyl |
| 17 | OAcetyl | S,S | H | Benzyl | Benzyl |
| 18 | OH | S,S | H | Benzyl | Benzyl |

We claim:

1. A compound of the formula I

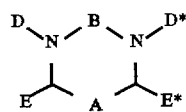 I in which A is a radical of the formula IIa,

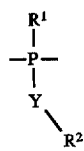 IIa in which

Y is oxygen;
$R^1$ is oxygen;
$R^2$ is
hydrogen,
$(C_1-C_6)$-alkyl,
$(C_7-C_{13})$-arylalkyl,
$(C_6-C_{12})$-aryl,
all of which are unsubstituted or substituted by hydroxyl, $(C_1-C_{10})$-alkyl, $(C_1-C_3)$-alkoxy, F, Cl or Br;
an equivalent of a physiologically tolerated salt, or
a residue of a phosphinic acid prodrug;
B is a radical of the formula IIIa

 IIIa where L is oxygen;
D and D* are, independently of each other,
$R^6\{(C_1-C_6)\text{-alkyl}\}$,
where the alkyl is saturated or unsaturated, branched or unbranched,
where $R^6$ is
$(C_6-C_{12})$-aryl, unsubstituted or substituted by $R^7$; or
$(C_3-C_{12})$-cycloalkyl, unsubstituted or substituted by $R^7$;
where $R^7$ is, independently of each other,
—$R^8$ where $R^8$ is
hydrogen, or
$(C_1-C_6)$-alkyl, unsubstituted or substituted by hydroxyl;
E and E* are benzyl.

2. A compound of the formula I as claimed in claim 1, in which A is a radical of the formula IIa, $R^2$ is
hydrogen,
$(C_1-C_4)$-alkyl,
an equivalent of a physiologically tolerated salt, or
a residue of a phosphinic acid prodrug;
D and D* are, independently of each other, $R^6$ —$CH_2$—,
where $R^6$ is $(C_6-C_{12})$-aryl which is unsubstituted or substituted once by $R^7$,
where $R^7$ is
—$R^8$,
—F, —Cl or —Br, where
$R^8$ is
hydrogen,
$(C_1-C_6)$-alkyl which is unsubstituted or substituted by hydroxyl or Br, and
E and E* are benzyl.

3. A compound of the formula 1 as claimed in claim 1, in which
$R^2$ is
hydrogen,
$(C_1-C_4)$-alkyl, or
an equivalent of a physiologically tolerated salt,
and D is benzyl which is substituted by $R^8$, where
$R^8$ is hydrogen,
$(C_1-C_3)$-alkyl, unsubstituted or substituted by hydroxyl or Br.

4. A process for preparing a compound of the formula I as claimed in claim 1, which comprises reacting a compound of the formula IV

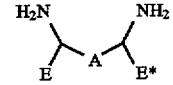 IV in which A, E and E* are as defined in claim 1, with an activated carbonic acid derivative or an oxalic acid derivative to form a cyclic urea or a cyclic oxalic acid diamide of the formula V

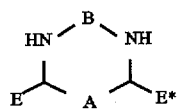 V in which A, E, E* and B are defined in claim 1 and said compound of the formula V is subsequently alkylated to form a compound of the formula I, or which comprises alkylating the compound of the formula IV to form an intermediate compound and subsequently cyclizing the intermediate compound to form a compound of the formula I.

5. A pharmaceutical composition comprising an effective quantity of at least one compound of the formula I as claimed in claim 1.

6. A process for preparing a pharmaceutical composition as claimed in claim 5, which comprises bringing an effective quantity of a compound of the formula I into a suitable form for administration together with customary pharmaceutical auxiliary substances.

7. A process for treating a disease responsive to aspartyl protease inhibition caused by a virus which process comprises administering an effective amount of a compound of the formula I as claimed in claim 1.

8. A process for treating a disease as claimed in claim 7, wherein said disease is caused by HIV.

* * * * *